(12) United States Patent
Gupta

(10) Patent No.: US 10,166,259 B1
(45) Date of Patent: Jan. 1, 2019

(54) ISOLATION OF EXOSOMES FROM COLOSTRUM POWDER AND EXOSOMAL DRUG FORMULATIONS USING THE SAME

(71) Applicant: 3P Biotechnologies, Inc., Prospect, KY (US)

(72) Inventor: Ramesh Gupta, Prospect, KY (US)

(73) Assignee: 3P Biotechnologies, Inc., Prospect, KY (US)

( * ) Notice: Subject to any disclaimer, the term of this patent is extended or adjusted under 35 U.S.C. 154(b) by 0 days.

(21) Appl. No.: 15/458,552

(22) Filed: Mar. 14, 2017

Related U.S. Application Data

(60) Provisional application No. 62/308,359, filed on Mar. 15, 2016.

(51) Int. Cl.
| | |
|---|---|
| *A61K 9/16* | (2006.01) |
| *A61K 31/12* | (2006.01) |
| *A61K 35/20* | (2006.01) |
| *A61K 9/127* | (2006.01) |

(52) U.S. Cl.
CPC ............ *A61K 35/20* (2013.01); *A61K 9/1276* (2013.01); *A61K 9/16* (2013.01); *A61K 31/12* (2013.01)

(58) Field of Classification Search
None
See application file for complete search history.

(56) References Cited

FOREIGN PATENT DOCUMENTS

WO   WO-2014-134132   *  9/2014

OTHER PUBLICATIONS

Total Water (https://www.total-water.com/blog/deionized-water-di-water/, Dec. 22, 2014).*
Staubach et al (Journal of Proteome Research, 2012, 11, 906-916).*
McGrath B, Dairy Science and Technology, 96(2), 133-158; (Year: 2016).*
Csapo J, International Dairy Journal, 6(8-9), 881-902 (Year: 1996).*
Raiha N, Nestle Nutrition Workshop, 33, 1994, 87-103. (Year: 1994).*

* cited by examiner

*Primary Examiner* — Celeste A Roney
(74) *Attorney, Agent, or Firm* — Law Office of J. L. Simunic; Joan Simunic

(57) ABSTRACT

A method for isolation of exosomes from bovine colostrum powder or goat colostrum powder, and the use of the isolated exosomes as nano carriers for small drug molecules, is described. Exosomes isolated from bovine colostrum powder averaged <85 nm in size, carried the surface-bound protein markers, Alix, TSG101, CD63 and CD81, and accepted various lipophilic (curcumin, withaferin A, paclitaxel) and hydrophilic (anthocyanidins) agents to serve as a nano carrier.

11 Claims, 2 Drawing Sheets

ISOLATION OF EXOSOMES FROM COLOSTRUM POWDER AND EXOSOMAL DRUG FORMULATIONS USING THE SAME

CROSS-REFERENCE TO PRIOR APPLICATIONS

The present application claims priority to U.S. Patent Application 62/308,359 filed 2016 Mar. 15, which is incorporated by reference in its entirety.

FIELD OF THE INVENTION

The invention relates to a method for isolating exosomes from colostrum powder and use of the isolated exosomes in drug formulations.

BACKGROUND OF THE INVENTION

Plant-derived bioactives have been used for decades for a variety of ailments. However, due to poor bioavailability high doses are required to elicit response, and the high doses may be toxic or may not be translatable to human use. Curcumin and green tea polyphenols represent some of the most investigated bioactives in both pre-clinical and clinical studies. Numerous formulations including liposomal, polymeric nanoparticles, micelles and emulsions have been reported for curcumin and other plant bioactives but none have met the clinical needs due to lack of scalability, costs and/or toxicity issues.

Chemotherapeutics are generally administered intravenously because of poor oral absorption/bioavailability. However, intravenous administration can cause blood spikes which may result in severe to life-threatening toxicities Taxanes are chemotherapeutics routinely used in the treatment of a broad spectrum of cancers, including lung, breast, ovarian, pancreas and cervical cancers. As with many other chemotherapeutic drugs, taxanes exhibit poor oral bioavailability; hence, they are administered intravenously, which is accompanied by spikes in blood levels, resulting in severe toxicities. Taxanes further suffer from having a low solubility and lack of long-term stability.

Oral chemotherapy offers many advantages over intravenous administration—including flexibility of timing and location of administration, flexibility of drug exposure, reduction of the use of the healthcare resources for in-patient and ambulatory-patient care services, and a better quality of life. However, the poor gastrointestinal absorption and hepatic first-pass effect related to many of these compounds means that bolus doses are required to achieve efficacy. To overcome this obstacle, several drug delivery systems have been developed, including liposomes, gold nanoparticles, carbon nanotubes, polymeric micelles, and polymeric implants. Of these, the liposomal delivery system has advanced the most: some chemotherapeutic drugs (e.g., doxorubicin) in liposomal formulations are already being used clinically, and a few others (cisplatin, oxaliplatin, and paclitaxel) are in Phase I/II clinical trials. However, without modification, these liposome formulations suffer from short-term blood-circulation time, instability in vivo, and a lack of target selectivity. Other limitations of liposomal systems include opsonisation and pharmacokinetic changes in multiple-dosing regimens.

Efforts to overcome these limitations have presented different challenges. For example, targeted liposomal formulations using immunoliposomes have been shown to improve efficacy; however, the immunoliposomes are rapidly eliminated from cells. Polymer-based delivery systems, including polymeric micelles, offer the advantages of linking various ligands to the surface; however, cost-effective, large-scale production and the elimination of toxicity remain elusive.

Recent studies have evaluated the use of exosomes as drug carriers. Exosomes are lipid-bilayer nanovesicles (30-100 nm) which are secreted by all cell types and occur naturally in such body fluids as blood, saliva, urine, and breast milk. In theory, exosomes have a) the potential to provide an appropriate drug delivery system due to their nano-scale size; b) a capability of loading both lipophilic and hydrophilic agents; c) the capacity to stabilize drugs, even in an acidic environment; and d) the potential ability to cross the blood brain barrier. By modifying membrane proteins, exosomes can become a desirable targeted-delivery approach.

Milk collected during day 1-2 after calving, the so-called colostrum, and mature milk contain a significant amount of exosomes and have been reported to carry a pay load of miRNAs, mRNAs, proteins and DNA. Exosomes isolated from milk can serve as a carrier of small therapeutic drugs and natural products, and milk-derived exosomes loaded with drugs have demonstrated significantly higher biological activities than naked drugs. In the past decade, standardized whole colostrum powder from bovine colostrum has become available commercially. Thus, it would be beneficial if an efficient means was available to isolate exosomes from this standardized whole colostrum powder.

SUMMARY OF THE PRESENT INVENTION

The present invention is a method for isolation of exosomes from bovine and goat colostrum powder, and use of the isolated exosomes as nano carriers for small drug molecules. The method comprises a predetermined series of sequential centrifugation steps, which result in the isolation of an abundance of exosomes which average <85 nm in size, carry the surface-bound protein markers characteristic of exosomes, and accept various lipophilic compounds to serve as a nano carrier.

DETAILED DESCRIPTION OF THE PRESENT DEVELOPMENT

Figure 1:
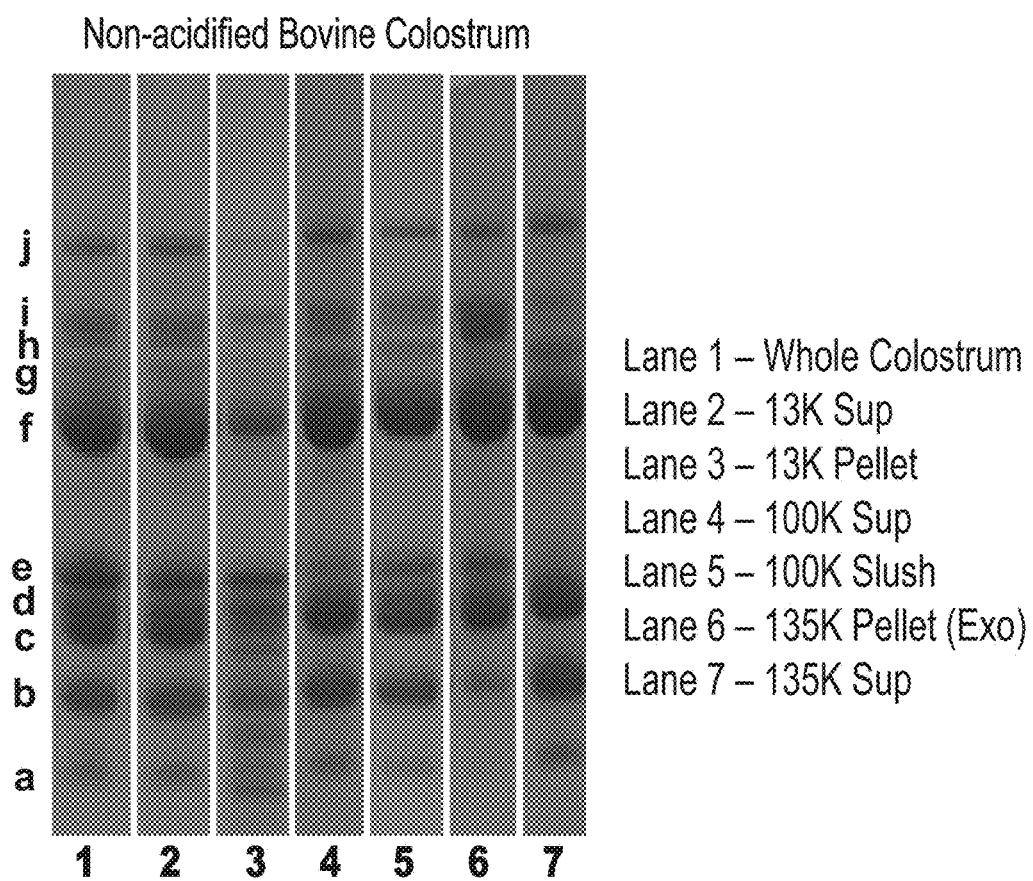
FIG. 1 is a collection of representative gels showing proteins from various fractions of bovine colostrum separated by polyacrylamide gel electrophoresis with coomassie staining; and, FIG. 2 is a collection of representative gels showing surface-bound exosomal proteins from colostrum-derived exosomes and milk-derived exosomes using the western blot method.

The present invention is a method for isolation of exosomes from bovine and goat colostrum powder, and use of the isolated exosomes as nano carriers for small drug molecules. The method for isolation of purified exosomes from colostrum powder comprises (a) providing a sample of colostrum powder; (b) suspending the colostrum powder in water and agitating to produce a uniform suspension; (c) subjecting the colostrum powder suspension to centrifugation at a first predetermined G-force; (d) collecting the supernatant from step (c); (e) subjecting the supernatant from step (d) to centrifugation at a second predetermined G-force; (f) collecting the supernatant from step (e); (g) subjecting the supernatant from step (f) to centrifugation at a third predetermined G-force; (h) collecting the exosomal pellet from step (g); (i) washing the exosomal pellet in de-ionized water; and, (j) suspending the exosomal pellet which contains the isolated purified exosomes in phosphate-buffered-saline (PBS). The isolated exosomes are loaded with small drug molecules by (a) combining isolated purified exosomes and a preselected drug in an organic solvent; (b) incubating the reaction mixture at a predetermined temperature and for a predetermined period of time; (c) subjecting the exosome-drug mixture to centrifugation at a first predetermined G-force; (d) collecting the supernatant from step (c); (e) subjecting the supernatant from step (d) to centrifugation at a second predetermined G-force; (f) collecting the exosomal pellet from step (e) and suspending the exosomal pellet in phosphate-buffered-saline (PBS); (g) subjecting the PBS suspension pellet to centrifugation at a third predetermined G-force; (h) collecting the supernatant which contains exosomes embedded with the drug from step (g). Optionally, the drug-embedded exosomes may be stored at −80° C. or lyophilized in the presence of mannitol, sucrose or trehalose.

The details of one or more embodiments of the presently-disclosed subject matter are set forth in this document. Modifications to embodiments described in this document, and other embodiments, will be evident to those of ordinary skill in the art after a study of the information provided herein. The information provided in this document, and particularly the specific details of the described exemplary embodiments, is provided primarily for clearness of understanding and no unnecessary limitations are to be understood therefrom. In case of conflict, the specification of this document, including definitions, will control.

Focusing initially on the method for isolation of purified exosomes from colostrum powder, the method comprises a multistep process. In order to most efficiently isolate quality exosomes, it is beneficial to start with a uniform suspension of an exosome-containing liquid. Fresh colostrum is originally in liquid form, but standardized powdered colostrum must be combined with water and agitated to produce a uniform suspension. Various methods to agitate the water—colostrum powder mixture are known in the art and any method that results in an essentially uniform suspension without denaturing the proteins in the colostrum powder may be used.

The colostrum powder suspension is then centrifuged to remove fat, cells, cell debris and insoluble proteins including casein. In a preferred embodiment, for this first centrifuge step, the suspension is centrifuged at about 13,000×g or 13K at a temperature of about 22° C.-23° C. for about 30 minutes. However, the specific acceleration, temperature and time may vary. For the purposes of isolating exosomes from colostrum powder, the acceleration may range from about 10,000×g to about 20,000×g; the temperature is preferably normal room temperature or from about 40° F. to about 80° F., and the centrifuge time is preferably between about 15 minutes to 120 minutes, and more preferably between about 15 minutes to 90 minutes.

The supernatant from the first centrifuge step is collected and transferred to a separate vessel. The supernatant is then subjected to a second centrifugation at a second predetermined G-force for a predetermined time to remove additional contaminants. In a preferred embodiment, for this second centrifuge step, the suspension is centrifuged at about 100,000×g or 100K at a temperature of about 40° F. for about 30 minutes. However, the specific acceleration, temperature and time may vary. For the purposes of isolating exosomes from colostrum powder, the acceleration may range from about 50,000×g to about 100,000×g, the temperature is preferably 35° F. to about 45° F., and the centrifuge time is preferably between about 30 minutes to 120 minutes.

About 70% of the supernatant from the second centrifuge step is collected and transferred to a separate vessel. This second supernatant is then subjected to a third centrifugation at a third predetermined G-force for a predetermined time to produce an isolated exosome pellet. In a preferred embodiment, for this third centrifuge step, the suspension is centrifuged at about 135,000×g or 135K at a temperature of about 40° F. for about 3 hours. However, the specific acceleration, temperature and time may vary. For the purposes of isolating exosomes from colostrum powder, the acceleration may range from about 120,000×g to about 180,000×g, the temperature is preferably from about 35° F. to about 45° F., and the centrifuge time is preferably between about 60 minutes to 8 hours.

The exosomal pellet is collected and washed with de-ionized water, and suspended in phosphate-buffered-saline (PBS) at about pH 7.4. The exosomal pellet may be used immediately or may be stored at temperatures of from about −20° C. or −80° C. for a period of at least 6 months.

To demonstrate the method for the isolation of exosomes according to the present invention, exosomes were isolated from bovine colostrum powder, caprine (goat) colostrum powder, fresh bovine raw milk, camel raw milk, and pasteurized and homogenized bovine whole milk. For studies using colostrum powder, suspensions of colostrum powder in deionized water were prepared by adding colostrum powder to deionized water and subjecting the mixture to constant shaking for about 60 minutes at room temperature or about 23° C. The fresh bovine raw milk, camel raw milk, and pasteurized and homogenized bovine whole milk were obtained in liquid form and were used as received.

Example 1

Suspensions of bovine colostrum powder are prepared so as to deliver 15 wt % colostrum (150 g colostrum powder per liter solution), 12.5 wt % colostrum, 10 wt % colostrum, 7.5 wt % colostrum, 6 wt % colostrum, and 5 wt % colostrum (50 g colostrum powder per liter solution). Each suspension is first centrifuged at about 13,000×g or 13K at about 22° C.-23° C. for about 30 minutes to remove fat, cells, cell debris and insoluble proteins including casein. The supernatant from each sample is transferred to a separate vessel and then centrifuged at about 100,000×g or 100K for about 30 min to remove additional contaminants. About 70% of the upper portion of each supernatant is collected and then centrifuged at about 135,000×g or 135K for about 3 hours to harvest the exosomal pellet. The pellet is washed with de-ionized water, and suspended in PBS, pH 7.4 and stored at −20° C. or −80° C. Exosomal pellets from samples having up to 7.5 wt % colostrum are transparent. Exosomal pellets from samples having 10 wt % colostrum or higher have a whitish color indicating the presence of more casein and other contaminants.

Example 2

The exosome isolation method of Example 1 is used with 5 wt % colostrum to isolate exosomes from bovine colostrum powder obtained from different batches and/or different suppliers. For demonstration purposes, thirteen replicates were run representing colostrum powder from two different sources and three different lots or batches. To allow for direct comparison, 2 L of 5 wt % colostrum suspension was used for each exosome isolation. In each case, the resulting exosome pellet obtained was largely transparent. Measurement of the protein content of the exosomes by standard BCA assay revealed that 2 L of 5 wt % colostrum (or 100 g colostrum powder) yielded about from about 1.2 g exosomal proteins or 1.2% to about 3.0 g exosomal proteins or 3.0%, with the average yield from the thirteen samples being about 2.1 g exosomal proteins or about 2.1%. The size and polydispersity index (PDI) of the isolated exosomes are measured by Zetasizer. The size of isolated exosomes ranged from about 56.6 nm to about 74.7 nm.

Example 3

The exosome isolation method of Example 1 is used to isolate exosomes from caprine colostrum powder, except that the exosomal pellet was collected after about 2 hours of centrifugation at about 135K. The yield of exosomes from a 5% caprine colostrum suspension is about 0.52 g per 2 L or 100 g colostrum powder. Size of exosomes from caprine colostrum is about 86 nm with PDI of 0.311.

Example 4

The exosome isolation method of Example 1 is used except the 5 wt % bovine colostrum powder suspension is replaced with raw bovine whole milk. The exosomes pellets are highly transparent and yield about 0.62 g exosomal proteins per L of milk. Exosomes from bovine raw milk are about 102 nm in size.

Example 5

The exosome isolation method of Example 1 is used except the 5 wt % bovine colostrum powder suspension is replaced with pasteurized bovine whole milk. The exosome pellets are essentially opaque and yield about 0.52 g exosomal proteins per L of milk. Exosomes from the pasteurized bovine milk are about 174 nm in size.

Example 6

Example 5 is repeated with a different source of pasteurized bovine whole milk, and results in exosome pellets that are essentially opaque and yield about 0.44 g exosomal proteins per L of milk. Exosomes from pasteurized bovine milk are about 204 nm in size.

Example 7

The exosome isolation method of Example 1 is used to isolate exosomes from camel raw milk, except that the exosomal pellet is collected after about 2 hours of centrifugation at about 135K. The yield of exosomes from the camel milk is largely transparent and is about 0.65 g per 2 L. The size of exosomes from camel milk is about 90 nm with PDI of 0.196.

Based on these examples, it appears that bovine colostrum gives higher recovery of exosomal proteins than bovine milk. As is known in the art, 1 L of fresh bovine colostrum produces about 220 g dry mass or colostrum powder, and based on the results from Example 2 it has been found that about 1 L of 5 wt % bovine colostrum suspension or 50 g colostrum powder yields about 1 g exosomal proteins (average yield from 2 L of 5 wt % is about 2.1 g). Therefore, 1 L of fresh bovine colostrum can be expected to yield about 4.4 g exosomal proteins. As shown in Examples 4-6, bovine whole milk yields about 0.53 g per liter. Thus, about 8.3-times more exosomal proteins can be harvested from colostrum powder than from fresh bovine milk under the same experimental conditions.

The exosomal pellet is harvested by centrifuging at 135K and the centrifuge time may be varied depending on the desired yield. However, exosome size may decrease slightly with extended centrifuging at 135K.

Example 8

Exosomes are isolated from 2 L of a 5 wt % colostrum suspension prepared according to Example 1, except the 135K centrifugation time is about 1.5 hours and 1.17 g exosomal proteins are isolated. Continued centrifugation of the supernatant for an additional 1.5 hours yields an additional 0.54 g exosomal proteins. Continued centrifugation of the second supernatant for an additional 3 hours yields an additional 0.88 g exosomal proteins. Thus, the combined exosomal protein fraction in 6 h equals 2.59 g.

Example 9

Exosomes are isolated from 2 L of a 5 wt % colostrum suspension prepared according to Example 1, except the 135K centrifugation time is about 1 hours and 0.77 g exosomal proteins are isolated. The size of the isolated exosomes are measured by Zetasizer and equal about 81 nm.

Example 10

Exosomes are isolated from 2 L of a 5 wt % colostrum suspension prepared according to Example 1, except the 135K centrifugation time is about 3 hours and 2.33 g exosomal proteins are isolated. The size of the isolated exosomes are measured by Zetasizer and equal about 64 nm.

Example 11

Exosomes are isolated from 2 L of a 5 wt % colostrum suspension prepared according to Example 1, except the 135K centrifugation time is about 4 hours and 2.48 g exosomal proteins are isolated. The size of the isolated exosomes are measured by Zetasizer and equal about 61 nm.

To determine distribution of the key proteins present in bovine colostrum powder, the various fractions (13K supernatant, 13K pellet, 100K supernatant, 100K pellet, 135K supernatant, 135K pellet) from the bovine colostrum were resolved by 4%-12% polyacrylamide gel electrophoresis and protein bands were detected by coomassie staining. As shown in FIG. 1, the exosomal protein profiles from the different fractions of the exosome isolation process were found to be qualitatively similar but significant quantitative differences were noted in the key protein bands. As shown in Lane 1, bovine whole colostrum powder has three prominent proteins (bands c, f and h), two major casein protein components (d and e), and several other minor components (bands a, b, and g, l and j). As shown in Lane 6, when the exosomes are isolated and pelletized, the three prominent proteins are present in the pellet and some of the casein and the minor components are less prominent, confirming that the process of the present invention does not negatively impact the quality or quantity of the exosomes of interest. Specifically, the caseins (bands d and e) are substantially removed in the 13K and 100K pellets, and the major proteins (bands c, f, and g) seem to be intensified in the 135K isolated exosome pellet. It is known that bovine colostrum powder contains immunoglobulins (IGs)—IgG, IgA and IgM. When reference IgG was electrophoresed in parallel with the 135K exosomal fraction isolated from bovine colostrum, reference studies strongly suggest that the protein bands c and f are IgG and IgA, and band h appears to be related to heavy chain IgM. Further, when isolated exosomes were separated from free IGs and electrophoresed, the isolated exosomes showed the presence of typical IgG, IgA and IgM bands, indicating that these IGs were tightly bound to the exosomes. This is the first evidence that these IGs, the most noted immune function-related proteins are bound to the exosomes.

Figure 2:
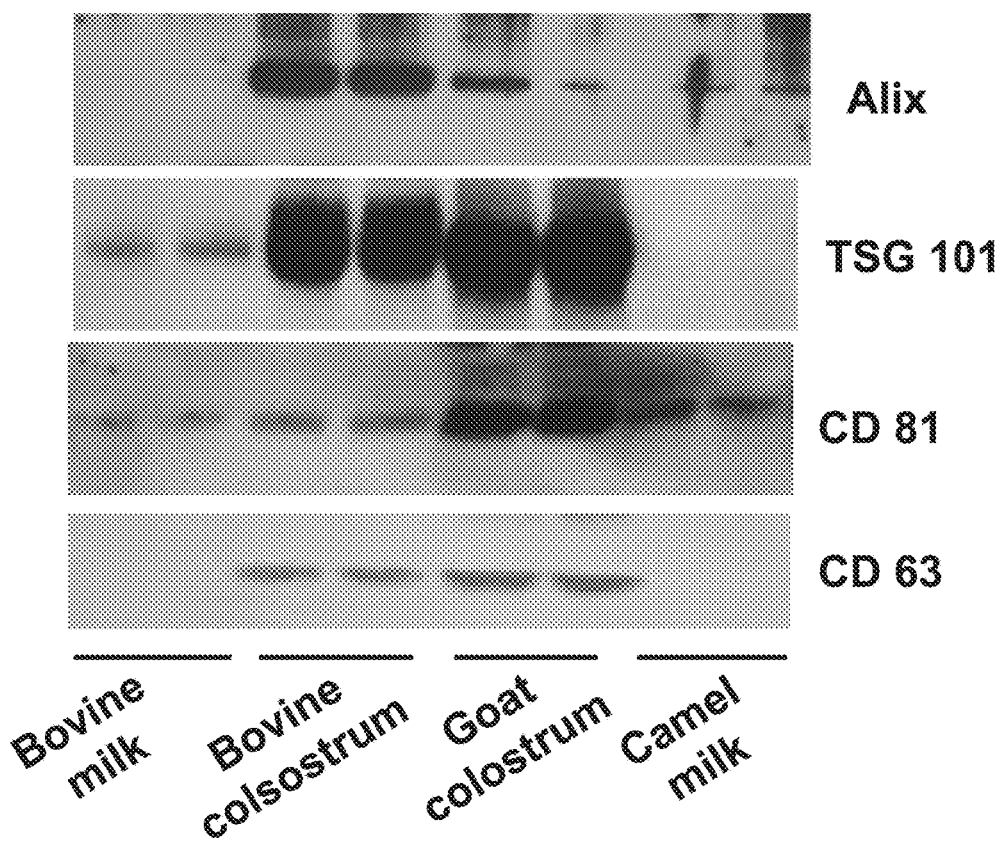

Numerous surface-bound proteins (Alix, Tsg101, CD81, CD63 etc.) are considered characteristics of exosomes. Therefore, exosomes isolated from bovine colostrum, goat colostrum, the raw and pasteurized bovine milk, and camel milk were analyzed by western blot by resolving on a 4%-12% polyacrylamide gel and then probed with antibodies for Alix, Tsg101, CD81 and CD63. As shown in FIG. 2, the colostrum exosomes, in general, had much higher levels of at least two surface-bound exosomal protein markers (Tsg101 and Alix); the exosomal protein markers in the milk-derived exosomes from bovine milk were present at substantially lower levels than colostrum exosomes; the levels in the pasteurized versus the raw milk were similar. The orders of these protein markers in the colostrum and milk-derived exosomes were as follows: Alix—bovine colostrum>>goat colostrum>camel milk>bovine milk; Tsg101—goat colostrum>bovine colostrum>>>bovine milk>camel milk; CD81—goat colostrum>>camel milk>bovine colostrum≈bovine milk; and CD63—bovine colostrum≈goat colostrum>>bovine milk≈camel milk. Based on the Alix data, it appears that the purity of exosomes isolated from the colostrum is at least 10-fold higher than milk exosomes, which should further increase the yield of exosomes from the colostrum compared with milk-derived exosomes.

The isolated exosomes can be loaded with small drug molecules, such as but not limited to various lipophilic agents and/or hydrophilic agents. Representative lipophilic agents include but are not limited to curcumin, withaferin A, and paclitaxel. Representative hydrophilic agents include but are not limited to the class of anthocyanidins.

The method for combining the isolated purified exosomes with the small molecules is a multistep process. Initially, the isolated purified exosome is combined with a preselected drug in an organic solvent to form an exosome-agent mixture. In a preferred embodiment, the organic solvent is ethanol or a 1:1 ethanol:acetonitrile blend. However, the organic solvent may be any solvent that will solubilize the drug agent without denaturing the exosome proteins and without decomposing the drug agent.

The exosome-agent mixture is incubated at a predetermined temperature and for a predetermined period of time. In a preferred embodiment, exosome-agent mixture is incubated at a temperature of about 22° C.-23° C. for about 20 minutes. However, the specific temperature and time may vary. For the purposes of loading a small molecule drug onto a colostrum-derived exosome, the temperature is preferably normal room temperature or from about 40° F. to about 80° F., and the incubation time is preferably between about 10 minutes to 90 minutes.

After the incubation period, the exosome-drug mixture is subjected to centrifugation at a first predetermined G-force. In a preferred embodiment, for this first centrifuge step, the mixture is centrifuged at about 13,000×g or 13K at a temperature of normal room temperature for about 15 minutes. However, the specific acceleration, temperature and time may vary. For the purposes of loading a small molecule drug onto a colostrum-derived exosome, the acceleration may range from about 10,000×g to about 20,000×g, the temperature is preferably normal room temperature or from about 40° F. to about 80° F., and the centrifuge time is preferably between about 10 minutes to 90 minutes.

The supernatant from the first centrifuge step is collected and transferred to a separate vessel. The supernatant is then subjected to a second centrifugation at a second predetermined G-force for a predetermined time. In a preferred embodiment, for this second centrifuge step, the mixture supernatant is centrifuged at about 135,000×g or 135K at a temperature of about 4° C. for about 90 minutes. However, the specific acceleration, and time may vary. For the purposes of loading a small molecule drug onto a colostrum-derived exosome, the acceleration may range from about 120,000×g to about 180,000×g, the temperature is preferably from about 35° F. to about 45° F., and the centrifuge time is preferably between about 45 minutes to 180 minutes.

Optionally, the second centrifuge step may use a selective filter, such as a MW-cutoff filter known in the art, with the acceleration adapted as appropriate for the selected filter. Further, the second centrifuge step may comprise a plurality of centrifuge runs, as may be required to remove the solvent.

The exosome-drug pellet is collected and suspended in PBS at about pH 7.4, and the PBS-suspended pellet is subjected to a third centrifugation at a third predetermined G-force for a predetermined time. In a preferred embodiment, for this third centrifuge step, the PBS-suspended pellet is centrifuged at about 13,000×g or 13K at a temperature of about 22° C.-23° C. for about 15 minutes. However, the specific acceleration, temperature and time may vary. For the purposes of loading a small molecule drug onto a colostrum-derived exosome, the acceleration may range from about 10,000×g to about 20,000×g, the temperature is preferably normal room temperature or from about 40° F. to about 80° F., and the centrifuge time is preferably between about 10 minutes to 30 minutes.

The supernatant which contains exosomes embedded with the drug is collected. The drug-embedded exosome may be used immediately or may be stored for a period of time or it may be lyophilized in the presence of mannitol, sucrose or trehalose. In an exemplary embodiment, the drug-embedded exosome may be stored at −80° C. for a period of at least 6 months.

To demonstrate the method for loading drug molecules onto the isolated exosomes according to the present invention, exosomes isolated from bovine colostrum powder were used. The following examples are for illustrative purposes only and are not intended to limit the scope of the invention. Examples 12-16 use curcumin, a commercially available mixture of three curcuminoids, a well-known anti-inflammatory plant-derived polyphenolic, as a model compound. However, it is anticipated that other compounds having similar chemical and physical characteristics to curcumin may be used and loaded onto the isolated exosomes according to the present method.

Example 12

Two mg of curcumin dissolved in ethanol:acetonitrile (1:1) is added slowly to 9 mg of exosome suspended in 2-ml of PBS, pH 7.4. Following incubation at room temperature (22-23° C.) for 10 min, the unbound curcumin is removed by low-speed centrifugation, leaving exosomes in supernatant. The supernatant is then centrifuged through a 10,000 MW-cutoff filter (Amicon Ultra-4) to remove the solvents. This process is repeated two more times following the addition of PBS for more complete removal of the solvents. The pellet comprising the drug-loaded exosome is then suspended in PBS. This procedure results in 65%-80% recovery of the exosomal proteins. To determine the drug load, an aliquot of the formulation is mixed with chilled ethanol and stored for about 1 h at −20° C., the supernatant was used to measure curcumin concentration by spectrophotometry while the pellet was dissolved in PBS to measure protein concentration. The drug load was calculated by dividing total curcumin in the formulation with the proteins×100, for a calculated drug load of 19%.

Example 13

Curcumin-loaded exosomes are prepared according to the procedure of Example 11 except that curcumin concentration is increased. Samples having a ratio of exosomes: curcumin at 3.5:1, 2:5:1, 1.2:1, 1:11:2, 1.3 and 1.4 are prepared and result in drug loads of 26%, 36%, 57%, 57% 81%, 75% and 25%, respectively.

Example 14

Curcumin-loaded exosomes are prepared according to the procedure of Example 11 except the exosomes:curcumin ratio is 2:1 and the exosomes are recovered by ultracentrifugation (135K) after 1½ hours and after 3 hours. The drug load is 43% (1.5 h) and 21% (3 h).

Example 15

Curcumin-loaded exosomes are prepared according to the procedure of Example 11 except the exosomes:curcumin ratio is 2:1 and the samples are incubated at 22-23° C. for 1 hour and 2 hours instead of 20 minutes, and then the exosomes are harvested by ultracentrifugation. The drug load in the samples incubated up to 1 h is the comparable to samples incubated for 20 minutes, but significantly lower drug load is observed after 2 hour incubation.

Example 16

Curcumin-loaded exosomes are prepared according to the procedure of Example 11 except the exosomes:curcumin ratio is 1:1 and the concentrations of the exosomes varies as 2 mg/ml, 1 mg/ml, 0.5 mg/ml and 0.2 mg/ml, and the exosomes are recovered by ultracentrifugation. The drug load for the 2 mg/ml samples and for the 1 mg/ml samples are similar, but the drug load declines with lower exosome concentration.

Other small drug molecules, withaferin A (WFA), bilberry-derived native mixture of anthocyanidins (Anthos), and the chemotherapeutic drug, paclitaxel (PAC), have been loaded onto isolated exosomes. Incubation of bovine colostrum-derived exosomes with WFA, Anthos, and PAC in a ratio of 4:1 or 1:1, followed by harvesting of the exosomes by the molecular filtration system result in high exosomal protein recovery (60-80%) but the drug load is relatively low—3-4% with WFA and Anthos, 6-8% for PAC, and the drug load seemed to be independent of the exosomes to drug ratios. However, when the exosomes were harvested by the ultracentrifugation procedure (135K), a significantly higher drug load is found (15-50%) at the expense of much lower recovery of the exosomal proteins (10-25%) compared with the molecular filtration system. But the drug loading is reduced if the centrifugation is continued for a longer time (135 K, 3 h) but there is a concomitant higher recovery of the exosomal proteins. Like with exosomal-curcumin formulation, the drug load for PAC, WFA and Anthos was also higher in the exosomes harvested at early times (45 min and 1½ h) compared with a later time (3 h). These data again suggest that the exosomal-drug molecules can be separated from exosomes not bound to the drug, thus resulting in much higher drug load.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims. The term "ambient temperature" as used herein refers to an environmental temperature of from about 0° F. to about 120° F., inclusive.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

All compositional percentages used herein are presented on a "by weight" basis, unless designated otherwise.

It is understood that, in light of a reading of the foregoing description, those with ordinary skill in the art will be able to make changes and modifications to the present invention without departing from the spirit or scope of the invention, as defined herein. For example, those skilled in the art may substitute materials supplied by different manufacturers than specified herein without altering the scope of the present invention.

What is claimed is:
1. A method for isolation of purified exosomes from colostrum powder, the method comprising:
   a. providing a sample of either standardized bovine colostrum powder or standardized caprine colostrum powder;
   b. suspending the colostrum powder in water and agitating to produce a uniform suspension;
   c. subjecting the colostrum powder suspension to centrifugation at a first predetermined G-force to produce a first supernatant and collecting the first supernatant;
   d. subjecting the first supernatant from step (c) to centrifugation at a second predetermined G-force to produce a second supernatant and collecting the second supernatant;

e. subjecting the second supernatant from step (d) to centrifugation at a third predetermined G-force to produce an exosomal pellet and collecting the exosomal pellet;
f. washing the exosomal pellet in de-ionized water; and,
g. suspending the exosomal pellet which contains the isolated purified exosomes in phosphate-buffered-saline (PBS), wherein the purified exosome yield is at least 8-times greater than if the exosomes were isolated from milk.

2. The method of claim 1 wherein the method is performed at a temperature of from about 40° F. to about 80° F.

3. The method of claim 1 wherein the first predetermined G-force is between 10,000×g to 20,000×g.

4. The method of claim 3 wherein the first predetermined G-force is 13,000×g.

5. The method of claim 1 wherein the first centrifugation is performed for from 15 minutes to 120 minutes.

6. The method of claim 1 wherein the second predetermined G-force is between 50,000×g to 100,000×g.

7. The method of claim 6 wherein the second predetermined G-force is 100,000×g.

8. The method of claim 1 wherein the second centrifugation is performed for from 30 minutes to 120 minutes.

9. The method of claim 1 wherein the third predetermined G-force is between 120,000×g to about 180,000×g.

10. The method of claim 2 wherein the third predetermined G-force is 135,000×g.

11. The method of claim 1 wherein the third centrifugation is performed for from 60 minutes to 8 hours.

* * * * *